(12) United States Patent
Kotzev

(10) Patent No.: US 6,281,310 B1
(45) Date of Patent: *Aug. 28, 2001

(54) METHACRYLATED OR ACRYLATED CYANOACETATES AND THE ADHESIVES AND POLYMERS THEREOF

(75) Inventor: Dimiter Lubomirov Kotzev, Northants (GB)

(73) Assignee: Chemence, Inc., Alpharetta, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/131,671

(22) Filed: Aug. 10, 1998

Related U.S. Application Data

(60) Provisional application No. 60/055,790, filed on Aug. 15, 1997.

(30) Foreign Application Priority Data

Mar. 26, 1996 (GB) .................................................. 9606327

(51) Int. Cl.$^7$ ................................ C08F 2/00; C08G 63/00
(52) U.S. Cl. .......................... 526/213; 528/271; 528/274; 528/370; 528/422; 526/214; 526/215; 526/216; 526/318; 526/320; 526/323.1; 526/323.2; 524/81; 524/401; 522/24; 522/104

(58) Field of Search ..................................... 528/271, 274, 528/370, 422; 526/213, 214, 215, 216, 318, 320, 323.1, 323.2; 524/81, 401; 522/24, 104

(56) References Cited

U.S. PATENT DOCUMENTS 4,340,708 * 7/1982 Gruber ................................. 526/313

* cited by examiner

*Primary Examiner*—Samuel A. Acquah
(74) *Attorney, Agent, or Firm*—Brobeck, Phleger & Harrison, LLP

(57) ABSTRACT

A methyacryloyl or acryloyl derivative of an ester of cyanoacetic acid may be of the formula:

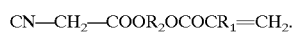

$R_1$ may be H or $CH_3$, and $R_2$ may be one of the group of moieties including alkyl, alkenyl, alkynyl, alkoxyalkyl, poly(oxyalkyl), aryl, cycloalkyl, and heterocyclyc radical, or substitited combinations thereof. Further, $R_2$ may include between 1 and 16 carbon atoms or heteroatom ring members.

19 Claims, 4 Drawing Sheets

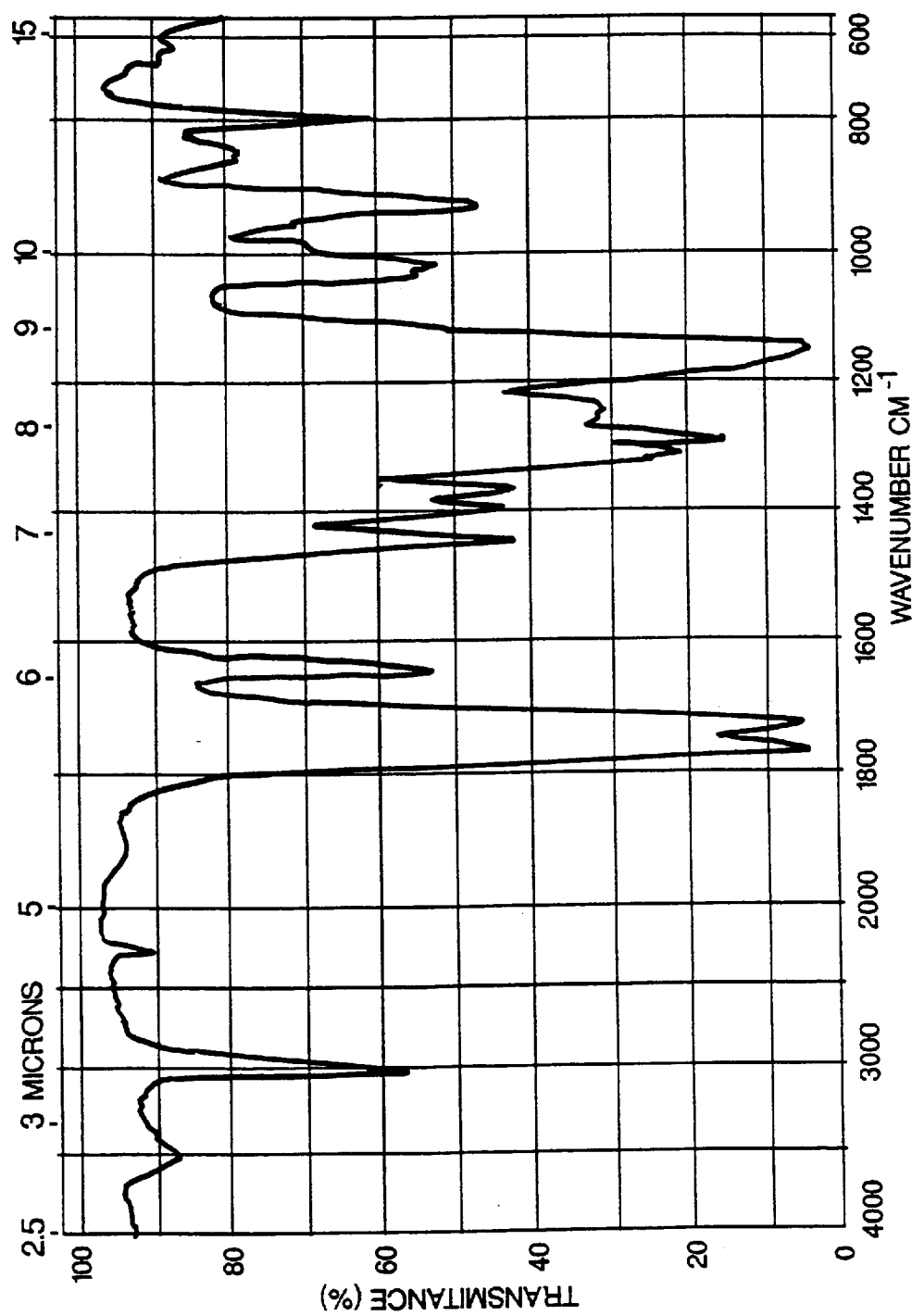
Fig. 1   IR spectrum of methacryloyloyloxyethyl cyanoacetate

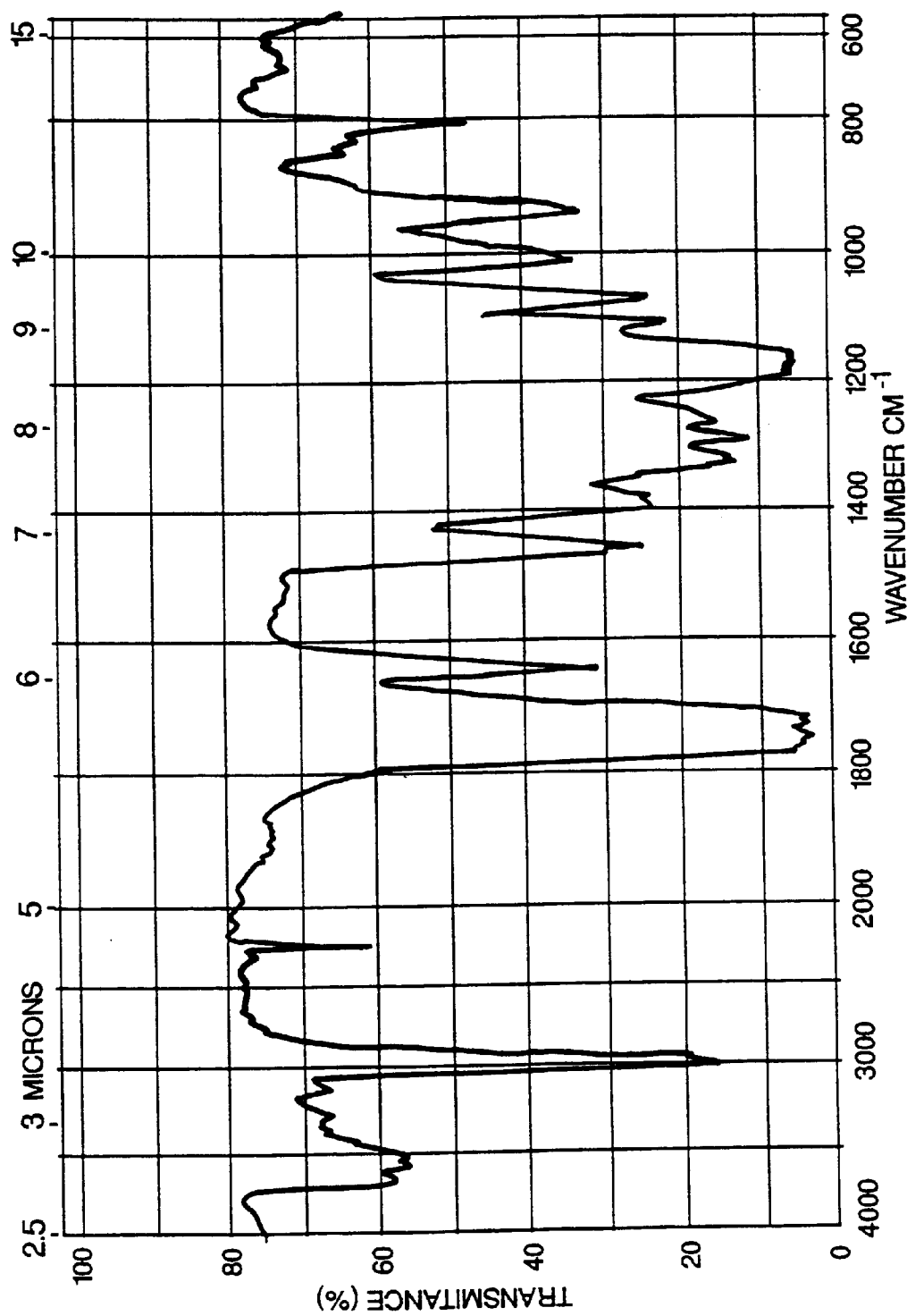
Fig. 2  IR spectrum of methacryloyloxypropyl cyanoacetate

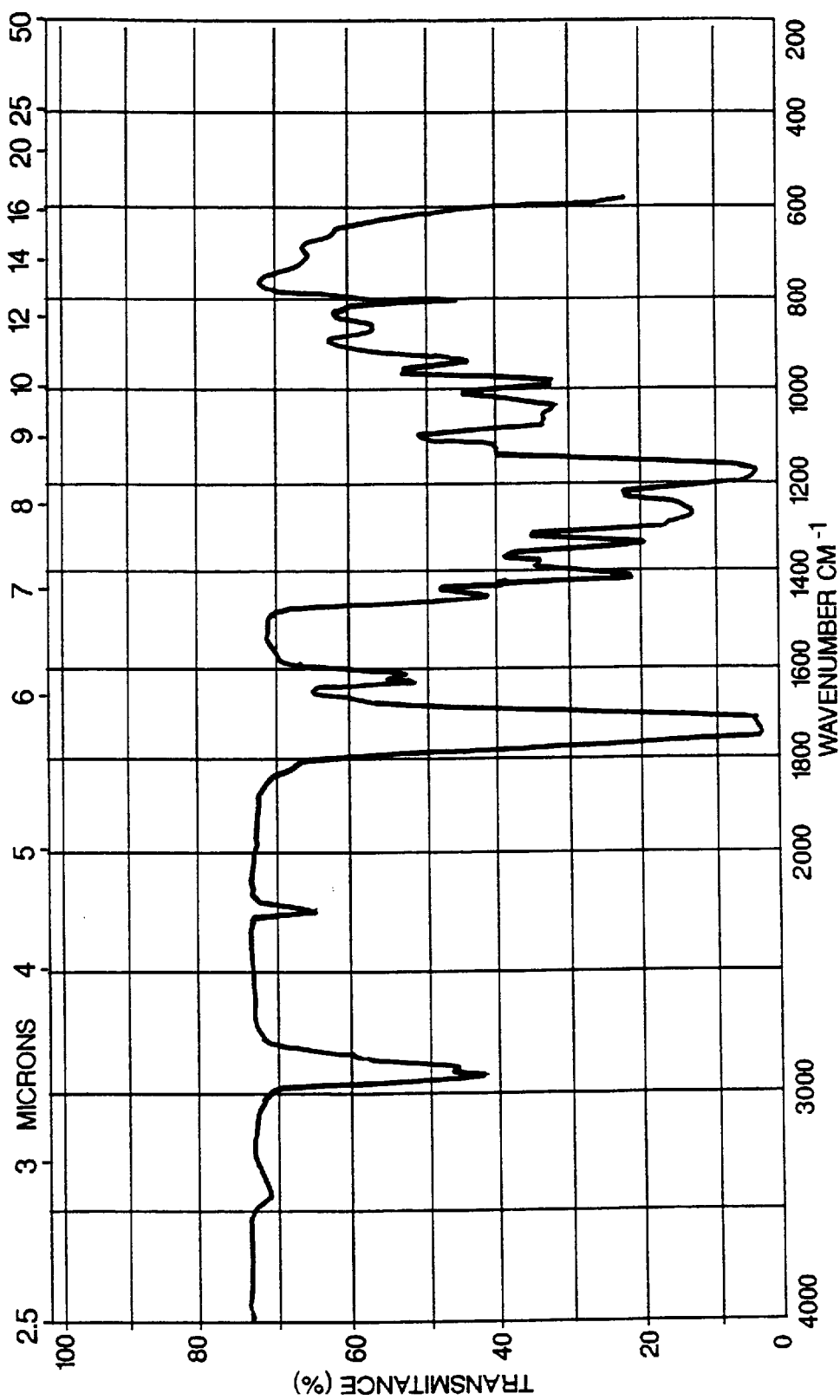
Fig. 3  IR spectrum of acryloyloxyethyl cyanoacetate

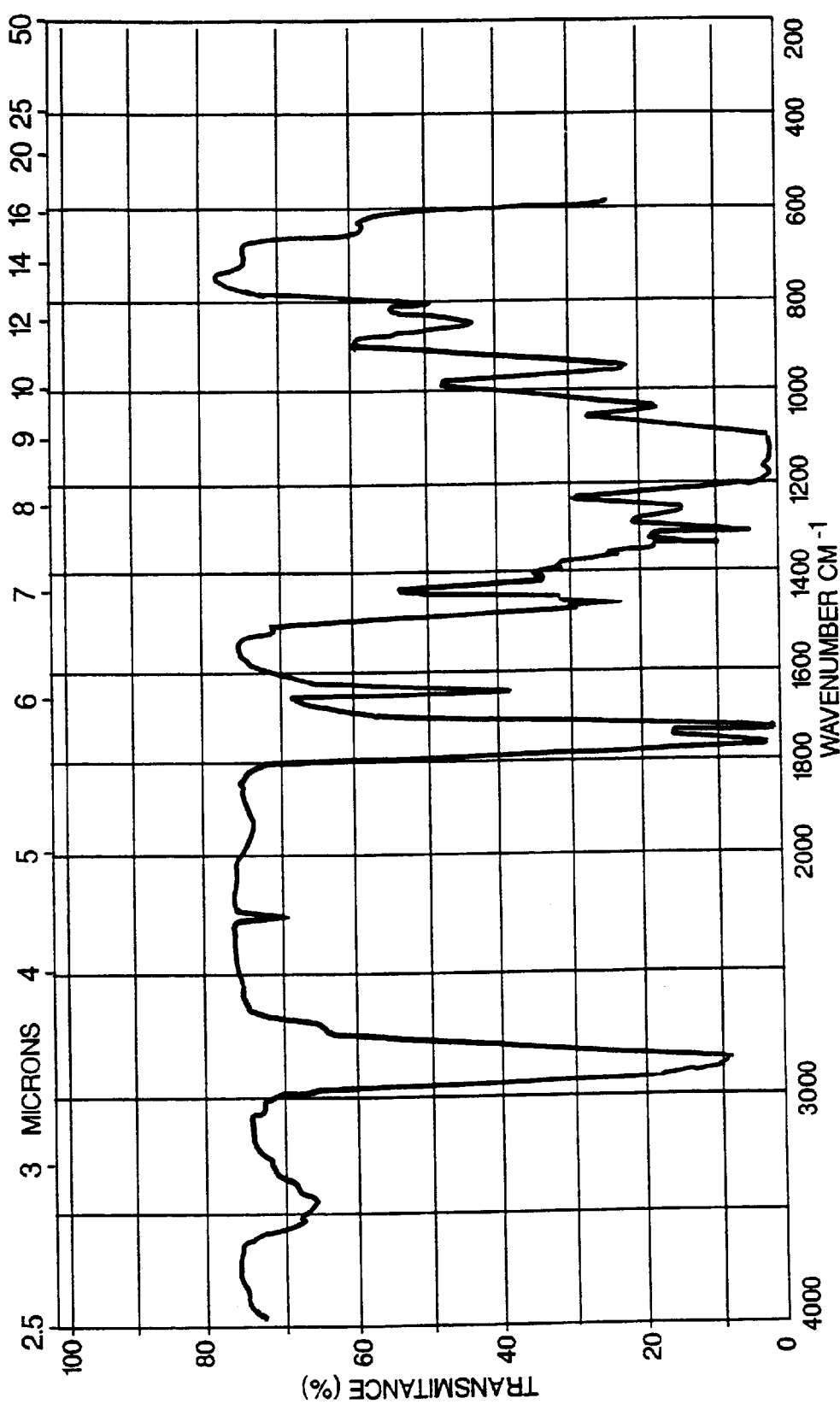
Fig. 4 IR spectrum of methacryloylhexa(oxyethyl) cyanoacetate

METHACRYLATED OR ACRYLATED CYANOACETATES AND THE ADHESIVES AND POLYMERS THEREOF

This application claims the benefit of Provisional 60/055,790 filed Aug. 15, 1997.

BACKGROUND OF THE INVENTION

1. Field of the Invention

This invention relates to methacrylated or acrylated cyanoacetates and the adhesives and polymers thereof.

2. Description of the Related Art

Cyanoacetic acid and its alkyl esters are used widely as raw materials for the synthesis of cyanoacrylate monomers and various pharmaceutical products.

SUMMARY OF THE INVENTION

The present invention provides methacryloyl or acryloyl derivatives of esters of cyanoacetic acid with formula

where $R_1$=H or $CH_3$, $R_2$ is alkyl, alkoxyalkyl, poly(oxyalkyl), cycloalkyl, alkynyl, aryl or an aromatic heterocyclic radical. $R_2$ may also be one of the foregoing moieties substituted with one or more other of the moieties; this includes the case of a substituent itself being substituted. Group $R_2$ may contain other compatible substituents, for example alkoxy, alkoxyalkoxy, carbalkoxyalkyl or halogen. The alkyl or alkenyl moiety may be cyclic and normally $R_2$ contains from 1 to 16 carbon atoms and often is a 1C, 2C, 3C, 4C, 5C, 6C, 7C or 8C group, more usually it is a 1C–6C group. In the case of moieties containing a heterocycle, heteroatom ring members are normally counted as a carbon atom.

BRIEF DESCRIPTION OF THE DRAWINGS

FIG. 1 depicts an infrared (IR) spectrum of methacryloyloxyethyl cyanoacetate.

FIG. 2 depicts an IR spectrum of methacryloyloxypropyl cyanoacetate.

FIG. 3 depicts an IR spectrum of acryloyloxyethyl cyanoacetate.

FIG. 4 depicts an IR spectrum of methacryloylhexa(oxyethyl) cyanoacetate.

DETAILED DESCRIPTION OF PREFERRED EMBODIMENTS

More preferably, $R_2$ is alkyl, halogenated alkyl, alkenyl, alkynyl, phenyl, halogenated phenyyl, phenyalkyl, halogenated phenylalkyl, alkoxyalkyl, alkoxyalkoxyalkyl, poly(oxyalkyl), carbalkoxymethyl or alkylideneglyceryl, wherein the terms "alkyl" and "alkenyl" include the corresponding cyclic radicals. Uninterrupted carbon chains preferably contain 1, 2 or 3 carbon atoms.

Specific examples of $R_2$ are:

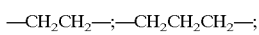

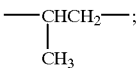

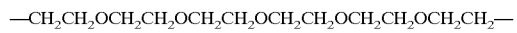

and

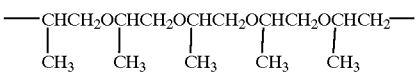

The methacrylated or acrylated cyanoacetates of this invention are obtained by two routes.

One is the esterification of cyanoacetic acid with hydroxyl-terminated methacrylate or acrylate monomer. The esterification process is well known in the art. It is catalysed by inorganic or organic acids. The water produced as reaction by-product is removed from the reacting mixture with the help of azeotrope-forming solvent. This drives the equilibrium reaction in the desired direction. The use of azeotrope-forming solvent is also beneficial in maintaining low reaction temperature.

The other route is transesterification of lower alkyl cyanoacetate with hydroxyl-terminated methacrylate and acrylate monomers. The transesterification process is well known in the art. It is catalysed by acids, alkali, organometalic compounds. The low molecular weight alcohol produced as reaction by-product is distilled out of the reacting mixture, driving the equilibrium reaction in the desired direction.

A distinctive feature of the reactions for obtaining the compounds of the present invention is the polymerizability of the methacrylate or acrylate reactant, as well as the end product itself. Thus in order to avoid polymerization during the reactions phenolic-type inhibitors, like hydroquinone or p-methoxyphenol, in conjunction with air sparge of the reacting mixture are used.

If desired mixtures of two or more of the cyanoacetates of the present invention with themselves or other monomers or polymers could be used.

Usually the methacrylated or acrylated cyanoacetates of the present invention are stabilized with free-radical polymerization inhibitors, usually hydroquinone, p-methoxyphenol or t-butyl catehol for example. The inhibitors are normally used in small amounts of from 0.001% to 1% by weight of the monomer. It should be noted that the quantity of inhibitor will influence not only the stability in bulk but also the onset of polymerization of the compounds of the present invention and could be used as a means to control the set time.

The methacrylated or acrylated cyanoacetates of the present invention may contain polymerization initiators. Free radical initiators like methylethylketone peroxide, cyclohexyl peroxide, cumene hydroperoxide, dibenzoyl peroxide etc and redoxy systems for generating free-radicals, well known in the art of polymerizing acrylate and methacrylate monomers, could be such polymerization initiators. Compounds which generate radicals under ultraviolet or electron beam irradiation could also be considered as suitable polymerization initiators of the monomers of the present invention. The various initiators could be used alone or in conjunction with each other.

In order to impart desired properties to the compounds of the present invention and to the properties of the resultant adhesive bond or polymer, as well as for economic considerations, further additives can be introduced. They can be, for example, any of the known polymeric thickness and viscosity regulators, rubbers, plasticizers and tougheners, compatibilizers, thixotropic agents, colourants, deodorants or perfumes, for example, used in cyanoacrylate adhesives and in acrylic and methacrylic ester compositions and polymers.

The compounds of the present invention may also contain other monomers containing a reactive double bond.

A distinctive feature of the methacrylated or acrylated cyanoacetates of the present invention is that they are easily polymerizable by heat, redoxy systems, ultraviolet or electron beam irradiation.

A distinctive feature of the methacrylated or acrylated cyanoacetates of the present invention is that due to the presence of the polar nitrile and carbonyl groups in their molecules the polymer formed interacts with the substrates it contacts during cure to form a strong adhesive bond.

A distinctive feature of the cyanoacetates of the present invention is that they contain an active methylene group which can react with ,β-unsaturated carbonyl compound, as acrolein, for example, to produce more complex monomeric molecules with multiple unsaturations.

Application of the monomers of the present invention is in adhesives and coatings.

Another application of the compounds of the present invention is in modifying existing adhesives and polymers.

Another application of the compounds of the present invention is as reactants for more complex compounds in which they incorporate acrylic or methacrylic double bond, nitrile and carbonyl groups.

The above mentioned applications are only indicative and do not limit the scope of application of the methacrylated or acrylated cyanoacetates of the present invention as well as the applications of their adhesives and polymers.

The invention is illustrated by the following examples:

EXAMPLE 1

134 g of hydroxyethyl methacrylate, containing 0.2 g of predissolved hydroquinone is mixed with 100 ml of heptane, 102 g of cyanoacetic acid and 2 g of sulfuric acid. An air flow of 10 ml/min is forced through a capillary in the bottom of the flask and maintained during the reaction. The temperature is brought to boiling and the reaction water is azeotroped into a Dean-Stark separator. The amount of removed water was used as measure of the completion of the reaction. 150 minutes after the start of reaction 17 ml of water were separated. The reaction mixture was cooled to room temperature. It separated in two layers. The upper heptane layer was decanted and 150 ml of methyl methacrylate were mixed with the product layer. The resultant solution was washed with 100 ml of 15% sodium chloride solution. The separated organic layer was neutralized to pH of 7 with 5% sodium carbonate solution and then washed again with 100 ml of 15% sodium chloride solution. The organic layer was filtered and stripped from heptane residues and methyl methacrylate by heating up to 90° C. under reduced pressure of 0.7 mm Hg. During the stripping stage an air sparge through a capillary was maintained. The residue was methacryloyloxyethyl cyanoacetate of which 192 g were obtained. Its refractive index at 200° C. was 1,4593 and was 99% pure by GC. The IR spectrum (FIG. 1) confirms the chemical structure.

EXAMPLE 2

74.4 g of hydroxypropyl methacrylate, containing 0.2 g of predissolved p-methoxyphenol, is mixed with 200 g of chloroform, 85.9 g of cyanoacetic acid and 3.4 g of sulfuric acid. An air flow of 5 ml/min is forced through a capillary in the bottom of the flask and is maintained during the run of the reaction. The temperature is brought to boiling and the reaction water is azeotroped into a Dean-Stark separator. The amount of removed water was used as measure of the completion of the reaction. 5 hours and 40 minutes after the start of the reaction 9 ml of water were separated. The reaction product was cooled to room temperature and consecutively washed with 200 ml water, neutralized to pH of 7 with 5% sodium hydroxide solution and then washed again with 200 ml of water. The organic layer was filtered and stripped from the chloroform solvent and water residues by heating up to 90° C. under reduced pressure of 0.7 mm Hg. During the stripping stage an air sparge through a capillary was maintained. The residue was methacryloyloxypropyl cyanoacetate of which 101 g were obtained. The refractive index at 20° C. was 1,4552. The product was 98% pure by GC and contained two isomers. The IR spectrum (FIG. 2) confirms the chemical structure.

EXAMPLE 3

46.5 g of hydroxyethyl acrylate, containing 0.1 g of predissolved p-methoxyphenol is mixed with 118.6 g of methyl cyanoacetate and 30 g of toluene. The mixture is brought to boiling at reduced pressure of 40 mm Hg and the toluene is distilled off removing with it any moisture present in the reactants. Sample of the resultant reaction mixture analysed by Karl-Fisher titration, shows water content of 0.04%. One gram of titanium tetraisopropoxide is added to the mixture and dry air sparging of 4 ml/min is initiated and maintained during the reaction. The mixture is brough to reflux at reduced pressure of 40 mm Hg. Methanol which is reaction by-product is removed from the reacting mixture by distillation. One hour after the reaction started the concentration of hydroxyethyl acrylate in the reacting mixture was reduced to 1% as determined by gas chromatograpahy. The heating was discontinued. 20 g of water were added and the reaction product was cooled down to room temperature. The added water reacted with the titanium catalyst precipitating it out of the reaction mixture. The water layer was decanted and the organic layer was filtered. The product was isolated from the excess of methyl cyanoacetate by vacuum distillation of the latter. After the end of visible distillation the product was kept for 30 minutes at 90° C. and 0.7 mm Hg. During the distillation and stripping stage a bleed of air was maintained through a capillary. The residue comprised of 61 g of acryloyloxyethyl cyanoacetate with GC purity of 97.7%. The refractive index at 20° C. was 1,4620 and the IR spectrum (FIG. 3) confirms the chemical structure.

EXAMPLE 4

87.7 g of hexaethyleneglycol monomethacrylate, containing 0.2 g of predissolved p-methoxyphenol is mixed with 100 g of chloroform, 25.5 g of cyanoacetic acid and 1.7 g of methanesulfonic acid. The next steps are identical to those described in Example 2 with the difference that the duration of the reaction was 5 hours and 5 minutes and 4.0ml of water were separated. The final yield of methacryloylhexa (oxyethyl) cyanoacetate was 86.4 g and had refractive index of 1,4674 at 20° C. The IR spectrum (FIG. 4) confirms the chemical structure.

EXAMPLE 5

UV light curable compositions were obtained by dissolving into various methacryloyl- and acryloylalkyl or poly-oxyalkyl cyanoacetates obtained by the methods described in Examples 1 to 4 of 1% by weight of 1-hydroxy-cyclohexyl-phenyl-ketone. A drop of the composition was spread between glass/glass or glass/steel surfaces and subjected to UV radiation with intensity of 7 mW/cm² at 365 nm and 4 mW/cm² at 310 nm for 2 minutes. Some of the joints were further aged at constant temperature for 24 hours. The glass and steel surfaces were only degreased with methylene chloride prior to bonding. The glass/glass joints and the glass portion of the glass/steel joints were in turn bonded in larger areas to steel coupons (with cyanoacrylate adhesive) so that they rather than the fragile glass could be gripped in the testing machine. The testing procedure followed ASTM D 1002 and ASTM D 807 respectively for the shear and tensile strength determinations. Each reported value is average of 10 determinations. The obtained results are summarized in Table 1.

TABLE 1

Adhesive bond strength of joints bonded with
UV-cured methacrylated and acrylated cyanoacetates

| No. | Cyanoacetate | Joint substrates | Mode of testing | Adhesive bond strength (kg/cm2) | Mode of failure |
|---|---|---|---|---|---|
| 1 | methacryloyl-oxyethyl | glass/glass | tensile | 78 | cohesive |
|   |   |   | shear | >20 | substrate |
|   |   | glass/steel | tensile | 78 | cohesive |
|   |   |   | shear | >20 | substrate |
| 2 | methacryloyl-oxypropyl | glass/glass | tensile | 36 | cohesive |
|   |   |   | shear | >20 | substrate |
|   |   | glass/steel | tensile | 43 | cohesive |
|   |   |   | shear | >20 | substrate |
| 3 | acryloyl-oxyethyl | glass/glass | tensile | 11 | adhesive |
|   |   |   | shear | 4 | cohesive |
|   |   | glass/steel | tensile | 10 | adhesive |
|   |   |   | shear | 7 | adhesive |
| 4 | acryloyl-oxypropyl | glass/glass | tensile | 5 | adhesive |
|   |   |   | shear | 2 | adhesive |
|   |   | glass/steel | tensile | 8 | adhesive |
|   |   |   | shear | 2 | adhesive |
| 5 | methacryloyl-hexa(oxyethyl) | glass/glass | tensile | 9 | cohesive |
|   |   |   | shear | 10 | cohesive |
|   |   | glass/steel | tensile | 8 | cohesive |
|   |   |   | shear | 9 | cohesive |
| 6 | methacryloyl-penta(oxypropyl) | glass/glass | tensile | 12 | cohesive |
|   |   |   | shear | 11 | cohesive |
|   |   | glass/steel | tensile | 13 | cohesive |
|   |   |   | shear | 12 | cohesive |

EXAMPLE 6

Adhesives based on pure ethyl 2-cyanoacrylate and ethyl 2-cyanoacrylate containing 1 to 10% by weight of some acryloyloxyalkyl and methacryloyloxyalkyl cyanoacetates were used to bond steel joints. The steel surfaces were roughened with extra fine sandpaper and degreased with methylene chloride. No chemical treatment of the surface was performed. A drop of adhesive was placed on one surface to which the other was manually pressed for 1 minute. Adhesive strength was measured 24 hours later. The specimen dimensions and testing procedure complied with ASTM D 897. Each reported value is average of 10 determinations. The obtained results are summarized in Table 2.

TABLE 2

Tensile strength of steel/steel joints bonded
with ethyl 2-cyanoacrylate compositions containing
methacrylated and acrylated cyanoacetates

| No. | Cyanoacetate | Content in the composition (%) | Adhesive strength (kg/cm²) |
|---|---|---|---|
| 1 | — | — | 120 |
| 2 | acryloyloxy-ethyl | 1 | 227 |
|   |   | 3 | 250 |
|   |   | 10 | 192 |
| 3 | acryloyloxy-propyl | 1 | 305 |
|   |   | 3 | 280 |
|   |   | 10 | 89 |
| 4 | methacryloyl-oxyethyl | 1 | 310 |
|   |   | 3 | 319 |
|   |   | 10 | 273 |
| 5 | methacryloyl-oxypropyl | 1 | 290 |
|   |   | 3 | 304 |
|   |   | 10 | 268 |

What is claimed is:

1. A methyacryloyl or acryloyl derivative of an ester of cyanoacetic acid of the formula:

$CN—CH_2—COOR_2OCOCR_1=CH_2$ wherein $R_1$ is H or $CH_3$, and $R_2$ is selected from the group of moieties consisting of alkyl, alkenyl, alkynyl, alkoxyalkyl, poly (oxyalkyl), aryl, cycloalkyl or heterocyclyc radical, or substitited combinations thereof and wherein said $R_2$ comprises between 1 and 16 carbon atoms or heteroatom ring members.

2. The ester of claim 1 wherein $R_2$ is:

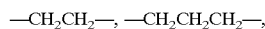
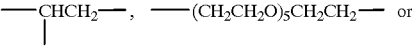
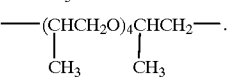

$—CH_2CH_2—, —CH_2CH_2CH_2—,$ $—\underset{\underset{CH_3}{|}}{C}HCH_2—, —(CH_2CH_2O)_5CH_2CH_2— \text{ or}$ $—(\underset{\underset{CH_3}{|}}{C}HCH_2O)_4\underset{\underset{CH_3}{|}}{C}HCH_2—.$ 3. An adhesive formed by the polymerization of one or more of the esters of claim 1.

4. An adhesive composition containing one or more of the esters of claim 1.

5. A method of synthesizing the ester of claim 1 by esterification of cyanoacetic acid with hydroxyl-terminated methacrylate or acrylate monomer.

6. A method of synthesizing the ester of claim 1 by transesterification of lower alkyl cyanoacetate with hydroxyl-terminated methacrylate or acrylate monomer.

7. A methyacryloyl or acryloyl derivative of an ester of cyanoacetic acid of the formula:

$CN—CH_2—COOR_2OCOCR_1=CH_2$ wherein $R_1$ is H or $CH_3$, and $R_2$ is selected from the group of moieties consisting of alkyl, alkenyl, alkynyl, alkoxyalkyl, poly (oxyalkyl), aryl, cycloalkyl or heterocyclyc radical, or substituted combinations thereof, and wherein said $R_2$ comprises between 1 and 16 carbons atoms or heteroatom ring members wherein said ester is stabilized against premature polymerization with one or more free-radical polymerization inhibitors, in amounts of from 0.001 to 1%.

8. The ester of claim 1 wherein said ester contains one or more polymerization initiators, said one or more polymerization initiators being selected from the group consisting of free-radical initiators, redoxy systems for generating free-radicals, or compounds which generate radicals under ultraviolet or electron beam irradiation.

9. A composition comprising one or more of the esters of claim 1, wherein said one or more esters further contains a monomer with a reactive bond.

10. Compositions comprising one or more of the esters of claim 1, said composition further comprising polymeric thickeners, viscosity regulators, plasticizers, thixotropic agents, compatibilizers, adhesion promoters, pigments, colorants, fillers, deodorants or perfumes.

11. A method for synthesizing a complex molecule comprising the step of reacting the ester of claim 1 with an $\alpha,\beta$-unsaturated carbonyl compound to produce a complex monomeric molecule with multiple unsaturations.

12. A method for improving adhesion comprising the step of adding the ester of claim 1 to an adhesive or a coating composition.

13. The ester of claim 1 wherein $R_2$ further comprises one or more halogens.

14. A polymer formed by the polymerisation of one or more of the esters of claim 1.

15. A coating composition comprising one or more of the esters of claim 1.

16. The ester of claim 7 wherein said one or more free-radical polymerisation inhibitors is selected from the group consisting of hydroquinone, p-methoxyphenol, t-butyl catehol, or combinations or mixtures thereof.

17. The ester of claim 8 wherein said free-radical initiator is selected from the group consisting of methylethylketone peroxide, cyclohexyl peroxide, cumene hydroperoxide, dibenzoyl peroxide or mixtures or combinations thereof.

18. The composition of claim 9 wherein said monomer is a cyanoacrylate.

19. A method for synthesizing a complex molecule comprising the step of reacting the ester of claim 1 to form a complex compound incorporating an acrylic or methacrylic double bond, a nitrile and a carbonyl group.

* * * * *